United States Patent [19]

Canavesi et al.

[11] Patent Number: 4,609,635

[45] Date of Patent: Sep. 2, 1986

[54] METHOD FOR THE REGENERATION OF AMMOXIDATION CATALYSTS

[75] Inventors: Roberto Canavesi, Arese; Ferdinando Ligorati, Usmate; Roberto Ghezzi, Cusano Milanino, all of Italy

[73] Assignee: Enichem Sintesi S.p.A., Palermo, Italy

[21] Appl. No.: 724,070

[22] Filed: Apr. 17, 1985

[30] Foreign Application Priority Data

Apr. 18, 1984 [IT] Italy ................................ 20587 A/84

[51] Int. Cl.$^4$ .................... B01J 27/28; B01J 38/66; B01J 38/60; C07C 120/02
[52] U.S. Cl. ........................................ 502/26; 502/27; 502/212; 558/462; 558/467
[58] Field of Search ....................... 502/27, 26, 25, 212

[56] References Cited

U.S. PATENT DOCUMENTS

| | | | |
|---|---|---|---|
| 2,973,326 | 2/1961 | Hodgins et al. | 502/25 |
| 4,052,332 | 10/1977 | D'Amore et al. | 502/27 |
| 4,410,450 | 10/1983 | Sasaki et al. | 502/27 |

*Primary Examiner*—P. E. Konopka

*Attorney, Agent, or Firm*—Hedman, Gibson, Costigan & Hoare

[57] ABSTRACT

Regeneration of an ammoxidation catalyst which is exhausted as a result of prolonged exposure to ammoxidation conditions, containing oxides of Mo, Bi, P, Fe, Co, Ni and possibly an alkali metal, particularly K, on a granular support, particularly silica, by means of a method including:

the impregnation of the granules of spent catalyst with an aqueous molybdic acid solution, or with an aqueous solution of partially or totally salified molybdic acid in the form of the ammonium salt, with a volume of impregnation solution less than the total pore volume of the catalyst subjected to regeneration;

the drying of the impregnated granules at a temperature of from 100° to 200° C.;

the calcining of the dried granules at a temperature of from 250° to 450° C., solely when the impregnation is with an aqueous solution of partially or totally salified molybdic acid.

Under ammoxidation conditions, the catalyst regenerated in this manner displays characteristics of activity, selectivity and of mechanical strength similar to those of the fresh catalyst.

10 Claims, No Drawings

METHOD FOR THE REGENERATION OF AMMOXIDATION CATALYSTS

DESCRIPTION

The present invention relates to a method of regenerating an ammoxidation catalyst constitued by metal oxides on a granular support, which is exhausted as a result of prolonged exposure to ammoxidation conditions.

Metal-oxide based, supported catalyst which are active in ammoxidation reactions, particularly in the production of acrylonitrile from propylene, ammonia and oxygen, are known in the art.

These catalysts, which initially contained oxides of Mo and Bi and possibly also P, were gradually improved and made more complex by the addition of oxides of other elements, such as Fe, Co and/or Ni and alkali metals. A typical catalyst used industrially in the production of acrylonitrile by the ammoxidation of propylene contains oxides of Mo, Bi, P, Fe, Co, Ni and K as the active part. The action of such a catalyst declines as a result of prolonged exposure to the ammoxidation conditions and this decline, which manifests itself mainly as a reduction in the yield of the useful reaction product given by the catalyst, is accompanied by a partial loss of the Mo content. Typically it is assumed that such an ammoxidation catalyst is spent, and hence needs regeneration, when, under the conditions for the ammoxidation of propylene, the yield of acrylonitrile with respect to the propylene converted is reduced by 5 or more percentage units compared with the value for the fresh catalyst. In the present text all the percentages are expressed by weight unless otherwise specifically indicated.

Several methods have been proposed in the art for the regeneration of spent ammoxidation catalysts and one of these methods, described in U.S. Pat. No. 3,882,159, is based essentially on a particular manner of restoring the lost Mo to the spent catalyst. More particularly, according to the specification of this patent, a molybdenum-impoverished, spent ammoxidation catalyst is brought into contact, under fluidization conditions, with fluidized particles constituted by $MoO_3$ deposited on an inert substrate. According to the specification of U.S. Pat. No. 4,052,332, spent ammoxidation catalysts are regenerated by a method which provides for their treatment with an aqueous solution containing soluble Mo and Bi salts, acidified with nitric acid.

The addition of Mo by the method of U.S. Pat. No. 3,882,159 is onerous and does not result in the satisfactory regeneration of the spent catalyst. On the other hand the regeneration method of U.S. Pat. No. 4,052,332 is not completely satisfactory in that the introduction of Bi (not lost to any noticeable extent under the ammoxidation conditions) into the spent catalyst together with the Mo varies the composition of the regenerated catalyst compared with the fresh catalyst and also introduces characteristics of fragility into the regenerated catalyst. In addition to this there are disadvantages in the use of nitric acid due to the evolution of nitrous vapours during the heat treatment of the catalyst being regenerated, and disadvantages due to the cost of the Bi salt.

According to the present invention, the spent ammoxidation catalyst is regenerated by the addition solely of the lost Mo to the catalyst by a particular method which gives the regenerated catalyst characteristics of activity, selectivity and mechanical strength equal to, or very close to, those of the fresh catalyst, thus avoiding the disadvantages of the prior art methods.

More particularly, according to the present invention, an ammoxidation catalyst constituted by a granular support, particularly silica, and by a catalytically active part, initially having the formula:

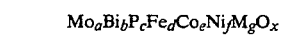

$Mo_aBi_bP_cFe_dCo_eNi_fM_gO_x$ where:
M is an alkali metal, particularly K, a is a number from 9 to 15,
b is a number from 0.3 to 2,
c is a number from 0.5 to 2,
d is a number from 1 to 5,
e is a number from 1 to 5,
f is a number from 1 to 5,
g is a number from 0.01 to 0.5,
x is a number such as to satisfy the valency requirements of the other elements, which is exhausted as a result of prolonged exposure to ammoxidation conditions, with the concommitant loss of from 2 to 10% of the initial Mo content, is regenerated by a method including:

impregnation of the granules of spent catalyst with an aqueous molybdic acid solution, or with an aqueous solution of partially or totally salified molybdic acid in the form of the ammonium salt, with a volume of impregnation solution less than the total pore volume of the catalyst subjected to regeneration, so as to restore at least 50% and up to 100% of the lost molybdenum;

drying of the impregnated granules at a temperature of from 100° to 200° C.;

calcining of the dried granules at a temperature of from 250° to 450° C., solely in the case of impregnation with an aqueous solution of partially or totally salified molybdic acid.

The impregnation stage may be repeated one or more times until the desired quantity of Mo has been restored to the spent catalyst. In such a case the granules are dried under the temperature conditions indicated above after each impregnation.

A general formula for the ammoxidation catalyst compositions which are subjected to the method of the present invention has been given above.

A typical, fresh ammoxidation catalyst has the following formula:

$Mo_{12.2}Bi_1P_{0.5}Fe_3Co_{4.5}Ni_{2.5}K_{0.07}$ and also contains oxygen in sufficient quantities to satisfy the valencies of the other elements. This catalytically active part represents about 50% by weight of the catalyst, the remaining percentage being constituted by a silica support in the form of granules having an average size of 50–70 micrometers. Under ammoxidation conditions in a cylindrical stainless steel pilot reactor having an internal diameter of 40 mm and a length of 1 m, such a catalyst typically gives a conversion of the propylene of the order of 91–93% with a selectivity towards acrylonitrile of the order of 78–80% with respect to the propylene supplied. After several months of use, the activity is of the order of 89–90%, the selectivity is of the order of 68–70% and the catalyst has lost about 7-10% of its Mo content and needs to be regenerated.

For this purpose, according to the method of the present invention, an aqueous solution of molybdic acid or an aqueous solution of partially or totally salified molybdic acid in the form of the ammonium salt is prepared.

The aqueous molybdic acid solution may be prepared by percolating an aqueous solution of an alkali metal molybdate through a strong cationic exchange resin, thus causing the molybdic acid to separate, as described for example in French Pat. No. 80026957. With this method it is possible to obtain aqueous molybdic acid solutions with Mo concentrations (evaluated as the metal) of the order of 80 g/liter.

Alternatively, an aqueous ammonium molybdate solution may be used, particularly ammonium heptamolybdate, $(NH_4)_6Mo_7O_{24}$, with an Mo concentration (evaluated as the metal) of more than 150 g/liter, given the greater solubility of the salt than the acid. Finally, aqueous solutions of partially salified molybdic acid in the form of the ammonium salt may be used, these being obtained for example by the addition of ammonia to the molybdic acid solutions described above. Conveniently, the aqueous solutions used for the impregnation contain a quantity of Mo (evaluated as the metal) of from about 50 to about 160 g/liter.

According to the present invention, the spent catalyst particles are impregnated with the aqueous solution of the Mo acid and/or salt and the use, in the impregnation, of a volume of impregnation solution less than the total pore volume of the catalyst subjected to regeneration is a critical aspect of the method of the present invention. The pore volume of the catalysts of the present invention is typically of from 0.2 to 0.3 ml/g.

Thus, in the case of a spent catalyst with a pore volume of 0.2 ml/g, the volume of solution usable for the impregnation is less than 200 ml/kg of catalyst. In the preferred embodiment, the volume of solution used for the impregnation is from 0.7 to 0.95 times the total pore volume of the spent catalyst.

In the practice, the impregnation may be carried out by pouring the solution of Mo acid and/or salt onto the spent catalyst particles kept in a fluidized state by means of a gas flow (air, nitrogen or oxygen).

This operation is conveniently carried out at low temperatures, for example at ambient temperature (20°–25° C.) or less, 10° C., or at temperatures slightly above the ambient and up to a maximum of the order of 40°–50° C. Alternatively the particles of spent catalyst are placed in apparatus of the powder-mixer type and the aqueous solution of Mo acid and/or salt is poured gradually onto the particles which are kept moving. The temperature range indicated above is used in this case as well.

At the end of the impregnation, the impregnated catalyst particles are dried at a temperature generally within the range 100° to 200° C. and preferably of the order of 140°–150° C. In practice, when the particles are fluidized, the drying may be carried out by increasing the temperature of the fluidizing gas suitably and when the operation is carried out in a mixer, a heating fluid may be passed into the jacket of the mixer itself.

The time needed for the drying may vary, generally from 0.5 to 5 hours, and is typically of the order of three hours.

Sometimes a single impregnation treatment carried out in the manner outlined above, will not restore the required quantity of Mo to the spent catalyst. In such a case the impregnation is carried out one or more times, the drying being effected after each impregnation, and the impregnation and the drying being carried out under the conditions already described.

In practice from 1 to 3 impregnations are used to add the required quantity of Mo to the catalyst to regenerate it, the number depending on the total pore volume of the spent catalyst subjected to regeneration and the Mo concentration in the solution used for the impregnation.

When the impregnation is carried out with an aqueous molybdic acid solution, the catalyst is regenerated after the drying and may be used immediately in the ammoxidation reaction. When the impregnation is carried out with an aqueous solution of partially or totally salified molybdic acid in the form of the ammonium salt, it is necessary to calcine the dried granules to a high temperature.

Temperatures suitable for this purpose vary within the range 250° to 450° C., with times from 3 to 5 hours.

Typical temperatures are of the order of 330°–350° C. with a typical time of the order of 4 hours. The heat treatment at high temperatures which is carried out in the presence of air may be carried out in the ammoxidation reactor itself.

With the method described above, it is possible to regenerate ammoxidation catalysts, restoring their activities, selectivities, and mechanical strengths to the values of the fresh catalysts. To this end it is essential to effect the impregnation of the granules of spent catalyst in the manner described above. It is in fact found that, when the impregnation is carried out with a quantity of Mo acid and/or salt solution greater than the total pore volume, a regenerated catalyst is obtained which is less selective towards the formation of the useful ammoxidation product and which has a more marked tendency to lose molybdenum during use.

The method of the present invention is simple and convenient and eliminates all the disadvantages of the prior art methods which used nitric acid or nitrates in the impregnation solution.

All this will become clearer from the experimental part which follows, which is given by way of example and without limiting the scope of the present invention.

A fresh ammoxidation catalyst is formed from a microspheroidal silica support and a catalytically active part (about 1:1 by weight). The catalytically active part can be defined by the formula:

$$Mo_{12.2}Bi_1P_{0.5}Fe_3Co_{4.5}Ni_{2.5}K_{0.07}$$

and also contains oxygen in quantities sufficient to satisfy the valencies of the other elements present.

The characteristics of this catalyst are as follows:

| | |
|---|---|
| grain size | 50–70 microns |
| bulk density | 0.9762 g/ml |
| specific surface | 23 m²/g |
| pore volume | 0.22 g/ml |
| molybdenum content | 20.5% by wt |

When this catalyst is tested in a tubular pilot reactor with an internal diameter of 40 mm under the following conditions:

| | |
|---|---|
| pressure | 0.88 bar |
| temperature | 440° C. |

| | |
|---|---|
| air supply | 130 N l/hour |
| propylene supply | 13.04 N l/hour |
| ammonia supply | |
| 530 g of fluidized catalyst with a contact time of 10 seconds (evaluated with empty reactor) at a temperature of 440° C. and a pressure of 0.88 bar: | |
| it gives the following results: | |
| conversion of the propylene | 92.5% |
| selectivity towards acrylonitrile | 79.0% |
| yield of acrylonitrile | 73.0% |
| yield of acetonitrile | 1.5% |
| yield of hydrogen cyanide | 4.0% |
| yield of CO + $CO_2$ | 13.5% |
| yield of other products | 0.5% |

The conversion relates to the supplied propylene, the selectivity towards acrylonitrile relates to the propylene supplied, and the yields of acrylonitrile and of the by-products relate to the propylene converted.

This catalyst, after several months of use in an industrial plant, has the following formula with reference to the catalytically active part:

$$Mo_{11.52}Bi_1P_{0.5}Fe_3Co_{4.5}Ni_{2.5}K_{0.07}$$

as well as oxygen in quantities sufficient to satisfy the valencies of the other elements.

The characteristics of this catalyst are:

| | |
|---|---|
| specific surface | 22 m²/g |
| pore volume | 0.20 g/ml |
| molybdenum content | 18.5% by weight |
| A sample of the catalyst tested in the pilot plant and under the conditions described above, gives the following results: | |
| conversion of the propylene | 89.3% |
| selectivity towards acrylonitrile | 68.5% |
| yield of acrylonitrile | 61.2% |
| yield of acetonitrile | 2.0% |
| yield of hydrogen cyanide | 7.5% |
| yield of CO + $CO_2$ | 17.1% |
| yield of other products | 1.5% |

The spent catalyst, impoverished in molybdenum, is subjected to regeneration in the experimental examples which follow.

EXAMPLE 1

958.5 g of spent catalyst (molybdenum content 18.5% by weight), having the characteristics given above, are fluidized by a flow of air introduced at the foot of a cylindrical glass reactor having an internal diameter of 40 mm and a height of 1 m.

An aqueous solution of molybdic acid having a molybdenum content, evaluated as the metal, of 60 g/liter is fed in dropwise from the head of the reactor. The molybdic acid solution was prepared from an aqueous sodium molybdate solution by percolation of the solution through the strong cationic exchange resin known commercially by the trade name DUOLITE C264 (made by the Chemical Process Company) in a manner similar to that described in Example 1 of French Pat. No.

160 ml of aqueous molybdic acid solution is dropped in from the head of the reactor over a period of about 30 minutes at ambient temperatures (20°-25° C.).

A quantity of aqueous molybdic acid solution is thus introduced in this phase which is about 83.5% of the total pore volume of spent catalyst. The drying is then carried out by raising the temperature of the fluidizing airflow to 150° C. and this temperature is maintained for the next three hours. The temperature is then returned to ambient values and a further 160 ml of aqueous molybdic acid solution (about 83.5% of the total pore volume) is fed in dropwise and the drying is then carried out in the manner described above. The temperature is again returned to ambient values and a further 141.5 ml (about 73.8% of the total pore volume) of an aqueous molybdic acid solution is dropped in and drying is carried out at 150° C. for four hours. Finally the reactor is cooled and the regenerated catalyst is discharged with a molybdenum content (expressed as the metal) of 20.5% by weight.

The regenerated catalyst is tested in the pilot plant and under the conditions previously described and gives the following results:

| | |
|---|---|
| conversion of the propylene | 92.0% |
| selectivity towards acrylonitrile | 78.4% |
| yield of acrylonitrile | 72.1% |
| yield of acetonitrile | 1.5% |
| yield of hydrogen cyanide | 5.0% |
| yield of CO + $CO_2$ | 12.9% |
| yield of other products | 0.5% |

These conversion, selectivity and yield values do not vary appreciably at the end of a test lasting 700 hours.

EXAMPLE 2

958.5 g of spent catalyst (molybdenum content of 18.5% by weight), having the characteristics given above, are placed in a powder mixer provided with a heating jacket.

160 ml of the aqueous molybdic acid solution having a molybdenum content (expressed as the metal) of 60 g/l described in Example 1 are dripped into the mixer, movement being maintained.

The operation is carried out with an addition time of 30 minutes, at ambient temperatures (20°-25° C.). The temperature is then brought to 150° C. by means of a fluid circulating in the heating jacket and this temperature is maintained for the next three hours. The reactor is cooled to ambient temperature, a further 160 ml of aqueous molybdic acid solution is added dropwise and drying is carried out at 150° C. in the manner described above. After the temperature has been returned to ambient values, a further 141.5 ml of aqueous molybdic acid solution is added dropwise and drying is finally carried out at 150° C. for 4 hours. The reactor is cooled and the regenerated catalyst is discharged with a molybdenum content (expressed as the metal) of 20.5% by weight.

The regenerated catalyst is tested in the pilot plant and under the conditions described above and gives the following results:

| | |
|---|---|
| conversion of the propylene | 91.6% |
| selectivity towards acrylonitrile | 78.5% |
| yield of acrylonitrile | 71.9% |
| yield of acetonitrile | 1.6% |
| yield of hydrogen cyanide | 4.8% |
| yield of CO + $CO_2$ | 12.8% |
| yield of other products | 0.5% |

After 200 hours, the molybdenum content of the catalyst is again equal to 20.5% by weight and no appreciable variations are noted with regard to its performance in the ammoxidation of propylene.

EXAMPLE 3

958.5 g of spent catalyst (molybdenum content of 18.5% by weight), having the characteristics previously described, are regenerated with the use of an aqueous molybdic acid solution which has been partially neutralised by the addition of aqueous ammonia. This solution has a molybdenum content (expressed as the metal) of 77 g/liter and an ammonium ion content (expressed as $NH_3$) of 22 g/liter.

Fluidization is carried out as described in Example 1, 180 ml of the solution (corresponding to about 94% of the total pore volume of the spent catalyst) being added dropwise in a first phase over a period of 30 minutes at ambient temperatures (20°–25° C.). After drying for 3 hours at 150° C., a further 180 ml of the solution is added dropwise in the manner described above. Finally, drying is carried out at 150° C. for three hours and the regenerated catalyst is kept at 350° C. for four hours.

The catalyst thus regenerated, the molybdenum content whereof (expressed as the metal) is 20.5% by weight, is tested in the pilot plant and under the conditions previously described and gives the following results:

| | |
|---|---|
| conversion of the propylene | 92% |
| selectivity towards acrylonitrile | 77.7% |
| yield of acrylonitrile | 71.5% |
| yield of acetonitrile | 1.6% |
| yield of hydrogen cyanide | 4.9% |
| yield of CO + $CO_2$ | 13% |
| yield of other products | 1% |

EXAMPLE 4

958.5 g of spent catalyst (molybdenum content of 18.5% by weight), having the characteristics described above, are regenerated with the use of an aqueous molybdic acid solution which has been partially neutralized by the addition of aqueous ammonia. This solution has a molybdenum content (expressed as the metal) of 154 g/liter and 23 g/liter of ammonium ions (expressed as $NH_3$).

Fluidization is carried out as described in Example 1, 180 ml of the solution (about 94% of the total pore volume of the spent catalyst) being added dropwise over a period of 45 minutes, at ambient temperatures (20°–25° C.). At the end of the impregnation, drying is carried out at 150° C. for three hours and heating is continued for the next four hours at 350° C.

The catalyst thus regenerated, the molybdenum content whereof (expressed as the metal) is 20.5% by weight, is tested in the pilot plant and under the conditions previously described and gives the following results:

| | |
|---|---|
| conversion of the propylene | 91.8% |
| selectivity towards acrylonitrile | 77.35% |
| yield of acrylonitrile | 71% |
| yield of acetonitrile | 1.7% |
| yield of hydrogen cyanide | 5.3% |
| yield of CO + $CO_2$ | 12.8% |
| yield of other products | 1% |

EXAMPLE 5 (CONTROL)

958.5 g of spent catalyst (molybdenum content of 18.5% by weight), having the characteristics described above, are regenerated by the general method of Example 2, the aqueous molybdic acid solution (molybdenum content, expressed as the metal, of 60 g/liter) being added in two successive portions of 231 ml (corresponding to 120% of the total pore volume of the spent catalyst). After each addition, which is carried out at ambient temperature (20°–25° C.) over a period of 45 minutes, the solution which has not been absorbed is drained off and drying is effected at 150° C. for three hours.

The regenerated catalyst obtained has a molybdenum content (expressed as the metal) of 20.3% by weight and is tested in the pilot plant and under the conditions previously described. The following results are obtained:

| | |
|---|---|
| conversion of the propylene | 92.3% |
| selectivity towards acrylonitrile | 76.4% |
| yield of acrylonitrile | 70.5% |
| yield of acetonitrile | 1.8% |
| yield of hydrogen cyanide | 5.0% |
| yield of CO + $CO_2$ | 14.0% |
| yield of other products | 1.0% |

After 200 hours, a sample of catalyst is taken and its molybdenum content is determined to be 20.1% by weight (expressed as the metal). Furthermore, the performance of t,e catalyst after this period of time is as follows:

| | |
|---|---|
| conversion of the propylene | 91.8% |
| selectivity towards acrylonitrile | 76.7% |
| yield of acrylonitrile | 70.4% |
| yield of acetonitrile | 1.8% |
| yield of hydrogen cyanide | 5.1% |
| yield of CO + $CO_2$ | 13.5% |
| yield of other products | 1.0% |

EXAMPLE 6 (CONTROL)

This is carried out as in Example 5, 958.5 g of spent catalyst being regenerated by means of an aqueous molybdic acid solution containing 65 g/liter of molybdenum (expressed as the metal). A regenerated catalyst is obtained with a molybdenum content of 20.5% by weight (expressed as the metal).

The performance of the catalyst initially is as follows:

| | |
|---|---|
| conversion of the propylene | 92.5% |
| selectivity towards acrylonitrile | 76.3% |
| yield of acrylonitrile | 70.6% |
| yield of acetonitrile | 1.6% |
| yield of hydrogen cyanide | 5.0% |
| yield of CO + $CO_2$ | 14.5% |
| yield of other products | 0.8% |

After 200 hours, the catalyst has a molybdenum content of 20.3% by weight (expressed as the metal) and its performance is as follows:

| | |
|---|---|
| conversion of the propylene | 91.9% |
| selectivity towards acrylonitrile | 76.6% |
| yield of acrylonitrile | 70.4% |
| yield of acetonitrile | 1.8% |
| yield of hydrogen cyanide | 5.0% |
| yield of CO + $CO_2$ | 13.7% |
| yield of other products. | 1.0% |

We claim:

1. Method for regeneration of an ammoxidation catalyst consisting of a granular support and a catalytically active part initially having the formula $$Mo_aBi_bP_cFe_dCo_eNi_fM_gO_x$$

where:
M is an alkali metal,
a is a number from 9 to 15,
b is a number from 0.3 to 2,
c is a number from 0.5 to 2,
d is a number from 1 to 5,
e is a number from 1 to 5,
f is a number from 1 to 5,
g is a number from 0.01 to 0.5,
x is a number such as to satisfy the valency of the other elements, which is spent as a result of prolonged exposure to ammoxidation conditions, with concommitant loss of from 2 to 10% of the initial Mo content, characterised in that:

the granules of spent catalyst are impregnated with an aqueous molybdic acid solution, or with an aqueous solution of partially or totally salified molybdic acid in the form of the ammonium salt, with a volume of impregnation solution less than the total pore volume of the catalyst subjected to regeneration, so as to restore at least 50% and up to 100% of the lost molybdenum;

the impregnated granules are dried at a temperature of from 100° to 200° C.;

the dried granules are calcined at a temperature of from 250° to 450° C. in the presence of air, solely in the case of impregnation by an aqueous solution of partially or totally salified molybdic acid.

2. Method according to claim 1, characterised in that the granules of the spent catalyst are impregnated one or more times and the granules are dried after each impregnation.

3. Method according to claim 1, characterised in that the impregnation is carried out at a temperature of from 10° C. up to 50° C.

4. Method according to claim 2, characterised in that the impregnation is carried out at a temperature of from 10° C. up to 50° C.

5. Method according to claim 1, characterised in that the impregnation is carried out with the catalyst particles kept under fluidized conditions.

6. Method according to claim 1, characterised in that the impregnation is carried out with the particles of the catalyst kept under movement in apparatus of the powder-mixer type.

7. Method according to claim 1, characterised in that the drying times vary from 0.5 to 5 hours.

8. Method according to claim 1, characterised in that the drying is carried out at temperatures of from 140° C. to 150° C. for a period of 3 hours.

9. Method according to claim 1, characterised in that the calcining is carried out for periods of from 3 to 5 hours.

10. Method according to claim 1, characterised in that the calcining is carried out at a temperature of from 330° C. to 350° C. for a period of 4 hours.

* * * * *